United States Patent
Morando

[11] Patent Number: 5,924,429
[45] Date of Patent: Jul. 20, 1999

[54] DISPOSABLE TOOTHBRUSH SYSTEM WITH INTEGRAL DENTAL FLOSS SUPPLY

[76] Inventor: Rudolph J. Morando, 55 Prospect Rd, Andover, Mass. 01810

[21] Appl. No.: 09/033,634
[22] Filed: Mar. 3, 1998
[51] Int. Cl.⁶ .................................................. A45D 44/18
[52] U.S. Cl. .......................... 132/309; 132/325; 132/311
[58] Field of Search .................................... 132/309, 308, 132/324, 325, 310; 206/368; 242/138, 146, 137.1; 221/30, 31, 32; 222/83, 83.5, 81

[56] References Cited

U.S. PATENT DOCUMENTS

| | | |
|---|---|---|
| 4,530,129 | 7/1985 | Labick et al. . |
| 4,865,481 | 9/1989 | Scales . |
| 4,919,156 | 4/1990 | Gipson . |
| 5,097,852 | 3/1992 | Wu . |
| 5,184,719 | 2/1993 | Gordon . |
| 5,304,009 | 4/1994 | Marshall . |
| 5,348,028 | 9/1994 | Gustavel . |
| 5,423,427 | 6/1995 | Brown . |
| 5,490,530 | 2/1996 | Snowden . |

*Primary Examiner*—Todd E. Manahan
*Assistant Examiner*—Eduardo C. Robert
*Attorney, Agent, or Firm*—Cesari and McKenna, LLP

[57] ABSTRACT

A dental-hygiene device is configured to receive a replaceable toothbrush and to provide a conveniently accessible source of dental floss. Generally, the device includes a handle for removably receiving a toothbrush, the handle defining an interior cavity; a supply of dental floss disposed within the interior cavity of the handle; provision for withdrawal of the dental floss through the handle; and a pivotable blade assembly, for separating a withdrawn length of dental floss from the supply.

5 Claims, 2 Drawing Sheets

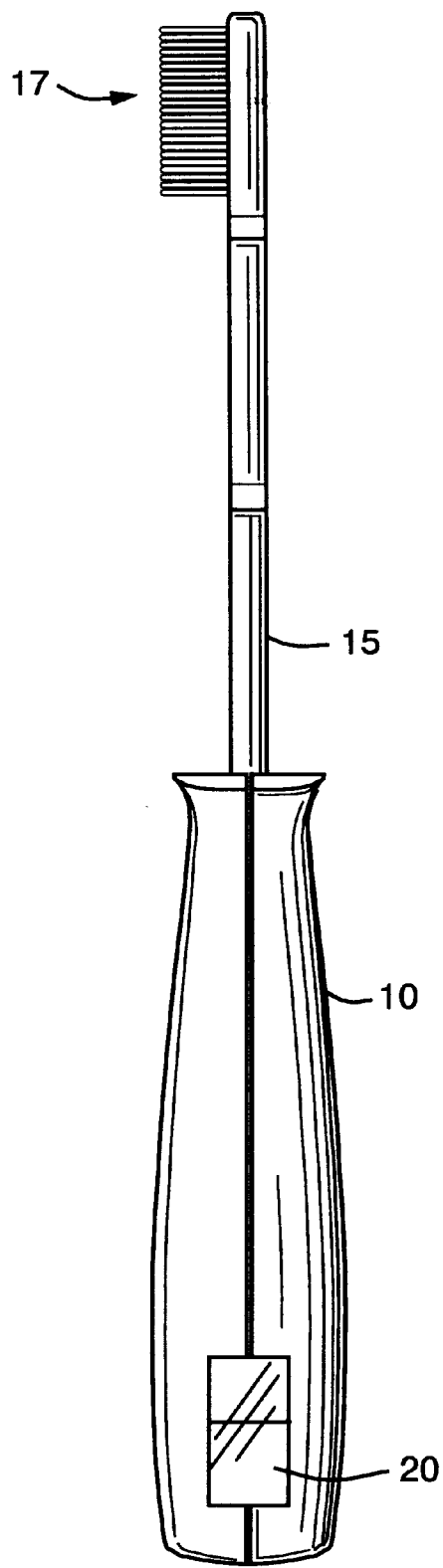
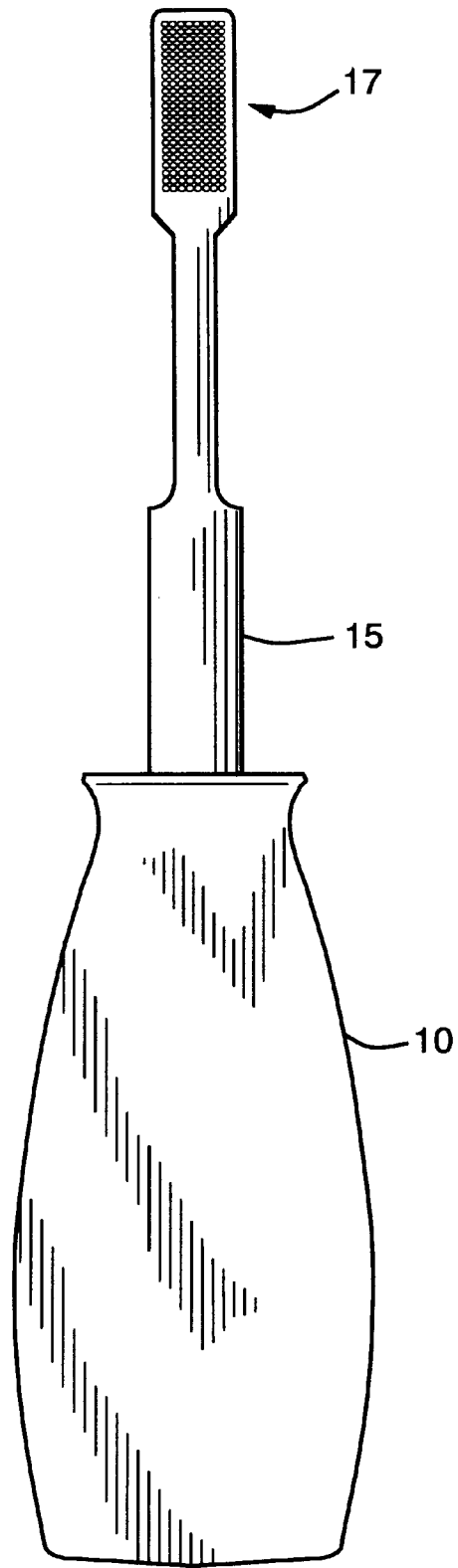
FIG. 1
FIG. 2

DISPOSABLE TOOTHBRUSH SYSTEM WITH INTEGRAL DENTAL FLOSS SUPPLY

BACKGROUND OF THE INVENTION

1. Field of the Invention

The present invention relates to dental-hygeine products, and in particular to a package for dispensing dental floss and accepting a series of disposable toothbrushes.

2. Description Of the Related Art

The traditional toothbrush consists of a generally elongate handle that terminates in an array of stiff bristles projecting at right angles to the handle. These bristles, usually made from a durable, flexible material such as nylon, are frequently rounded and tapered for user comfort and to encourage smooth brushing strokes.

Despite its mundane usage, the toothbrush has attracted substantial engineering attention in response to dental studies demonstrating persistent patterns of improper use and to accommodate particular dental conditions. For example, many toothbrushes now contain canted heads, wherein the portion of the handle bearing the bristles forms an angle with the remainder; this construction eases access to difficult-to-reach mandibular regions. Purchasers can choose among a range of bristle stiffness values, and the array of bristles may be tilted, beveled or otherwise shaped to increase cleaning efficacy.

Such advances have certainly reduced tooth decay among healthy consumer population, and reflect increased popular and medical attention to the benefits of dental hygeine. However, this very attention has also prompted recognition of the need to maintain the dental health of medically compromised patients—individuals for whom such care had once been considered extravagant. Thus, oncology patients now receive frequent dental examinations and tooth care, with the result that fewer such patients develop oral infections; and care providers regularly clean the teeth of convalescents and paralytics unable adequately to brush properly.

In a large institutional setting, such as a hospital, toothbrushes are frequently discarded after a single use. This practice avoids the spread of infection through inadvertent application of a single toothbrush to multiple patients, and reflects the impracticality of associating easily confused medical utensils with particular individuals. This practice is wasteful of toothbrushes that have been manufactured for extended use. Furthermore, since these toothbrushes are typically packaged individually, storage requirements for large patient populations can be considerable.

Cost and inconvenience may be increased further by the need to maintain toothbrushes having different constructions and bristle grades for different patient subsets.

In U.S. Pat. No. 5,414,890, I disclosed an interchangeable toothbrush system that affords the convenience of single-use brushes which may be received within a handheld base. This device does not, however, provide a convenient source of dental floss for use in conjunction with the toothbrush. If the benefits of flossing are to be realized, a supply of floss must be carried separately.

U.S. Pat. No. 5,348,028 describes a package having a handle capable of receiving a separable toothbrush and including an interior space for housing dental accessories including floss. To obtain access to the dental floss, however, a user must manually separate the handle into segments—an operation that is not only inconvenient, but can also tend to wear out the interfitting members that join the handle segments.

BRIEF SUMMARY OF THE INVENTION

The present invention provides a dental-hygiene device that is configured to receive a replaceable toothbrush and to provide a conveniently accessible source of dental floss. Generally, the invention comprises a handle for removably receiving a toothbrush, the handle defining an interior cavity; a supply of dental floss disposed within the interior cavity of the handle; means, such as an aperture, facilitating withdrawal of the dental floss through the handle; and means, such as a pivotable blade assembly, for separating a withdrawn length of dental floss from the supply.

The invention therefore combines the flexibility and economy of disposable toothbrushes with the convenience of an integral supply of dental floss. The brushes used in conjunction with the invention may contain fewer and/or less durable bristles compared with commercially marketed items, or may instead be configured for use on patients having special dental needs. The handle may, if desired, be designed to facilitate replacement of the supply of dental floss.

BRIEF DESCRIPTION OF THE DRAWINGS

The ensuing description of the invention will be understood more readily from the accompanying drawings, in which:

FIG. 1 is an elevational view of the invention from the side;

FIG. 2 is an elevational view of the invention from the front;

DETAILED DESCRIPTION OF THE PREFERRED EMBODIMENT

Refer first to FIGS. 1 and 2, which illustrate a handle 10 configured to removably receive a toothbrush 15. The bristles 17 of each brush are arranged in a pattern and suited to a particular usage. For example, in embodiments destined for institutional settings where each brush will be used but a single time, the bristles may be distributed less densely than would be the case in a standard commercial brush. Alternatively, the bristles may instead be arranged to accommodate or for treatment of particular dental conditions, such as gingivitis or periodontitis, along lines well-known to those skilled in the art. Alternatively, toothbrush 15 may be intended for long-term service and the invention employed for travel or ordinary household usage.

Figure 3:
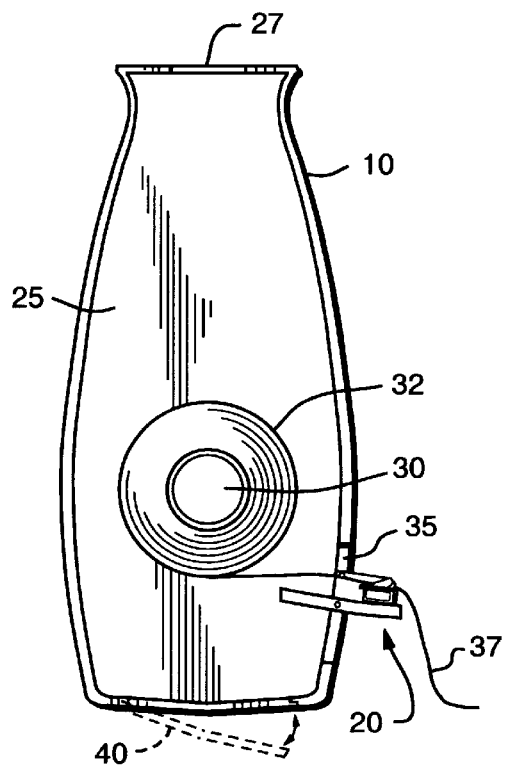
FIG. 3 is a cutaway depiction of the view shown in FIG. 1, illustrating the interior components of the invention, with the flip-out blade assembly in the open position.

Handle 10 also contains a flip-out blade assembly 20, described in greater detail below, positioned on the side of handle 10 toward the bottom. Handle 10 is generally contoured to fit within a user's hand. With reference to FIG. 3, handle 10 is largely hollow, defining an interior cavity 25. A toothbrush is received in a top slot 27, which is sized to permit the toothbrush to be force-fit therein for use but removable thereafter. During use, therefore, the shank of a toothbrush extends into interior cavity 25.

Cavity 25 contains a spool 30 around which a supply 32 of dental floss is wound. Spool 30 is free to rotate within cavity 25. Flip-out blade assembly 20 is pivotally mounted within the wall of handle 10. With assembly 20 in the open position, as shown, an aperture 35 is revealed through the wall of handle 10. A length 37 of dental floss from supply 32 may be received in aperture 35 and thereby withdrawn from handle 10. Handle 10 may also contain a hinged access door 40 that allows the user to remove and replace spool 30 when floss supply 32 becomes exhausted. For example, the ends of spool 30 may removably fit within complementary detents (not shown) in the interior walls of handle 10, allowing for removal of the empty spool and installation of a new floss supply. The unhinged end of door 40 may snap-fit into the bottom of handle 10, or may instead by opened or locked into a closed position by means of a spring-loaded tab.

Figure 4:
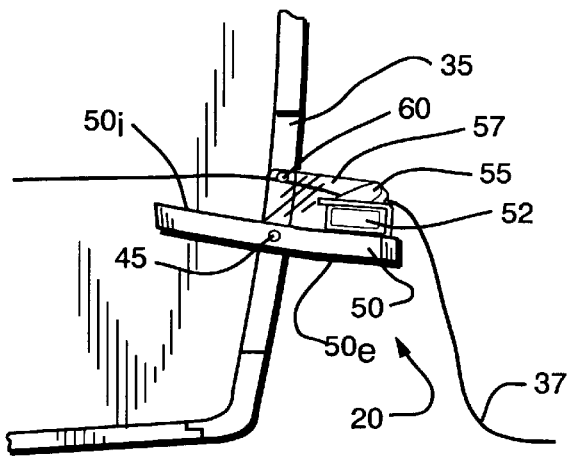
FIG. 4 is an enlarged view of the flip-out blade assembly.

With reference to FIG. 4, it is seen that assembly 20 is pivotable, as indicated by the arrow, about a stationary pin 45. Blade assembly 20 includes a cover 50 having interior and exterior surfaces 50i, 50e, respectively. Affixed to the interior surface 50i is a table 52; a blade 55 rising from table 52 (e.g., drawn up from the surface of table 52 as a sharp flap); and behind table 52, a guide wall 57 rising from surface 50i and including a guide pin 60. With assembly 20 in the illustrated open position, therefore, the user has convenient access to blade 55. Floss 37 may be withdrawn from supply 32 over table 52, its travel path being circumscribed by blade 55, guide wall 57 and guide pin 60. That is, guide wall 57 and guide pin 60 inhibit floss 37 from becoming wedged between cover 50 and the walls of aperture 35. When a sufficient length of floss has been withdrawn, the user simply tugs floss 37 across blade 55 (i.e., away from guide wall 57), which cuts the floss.

By virtue of its position within handle 10 and the manner in which it is hinged, assembly 20 alternates easily between the open and closed positions. The user may close assembly 20 merely by pressing his or her thumb against its exterior surface 50e. Cover 50 fits snugly within aperture 35 so that assembly 20 remains in the closed position until opened by the user. With assembly 20 closed, the exterior surface 50e follows the exterior surface contour of handle 10. Furthermore, because of the snug fit between cover 50 and aperture 35, closure of assembly 20 compresses the dental floss 37 received in the aperture to inhibit further withdrawal of the dental floss.

To open assembly 20, the user presses his or her thumb against the lower portion of exterior surface 50e. Cover 50 may pivot to a substantially horizontal position as illustrated or beyond this angle, allowing for convenient access to blade 55 with handle 10 held in the normal, upright position.

In an alternative embodiment, assembly 20 is located on the bottom of handle 10 rather than on the side. It should also be noted that the size of cover 50 can be varied depending on the access to be afforded to interior cavity 25.

Figure 5:
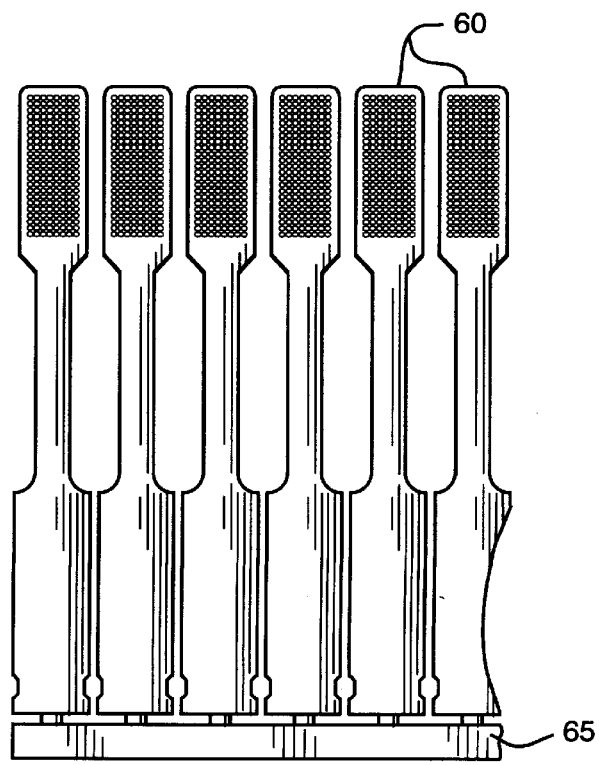
FIG. 5 is an elevational view showing how disposable toothbrushes useful in conjunction with the present invention may be manufactured in an array of detachable units.

Toothbrushes for use with the present invention may be easily manufactured in multiple-unit packages, thereby facilitating convenient use, removal, and replacement. One suitable configuration is disclosed in the '890 patent. Another approach is shown in FIG. 5, which illustrates a series of disposable toothbrushes 60 removably affixed to a common spine 65 by means of breakaway attachments. To remove one of the toothbrushes 60, it is simply twisted, thereby breaking the deliberately weak attachment to spine 65.

Accordingly, it will be seen that I have invented a multipurpose dental-hygiene arrangement that accommodates toothbrushes and dental floss, and that my design is capable of being implemented in a variety of ways. The terms and expressions employed herein are used as terms of description and not of limitation, and there is no intention, in the use of such terms and expressions, of excluding any equivalents of the features shown and described or portions thereof, but it is recognized that various modifications are possible within the scope of the invention claimed.

What is claimed is:

1. A dental-hygiene device comprising:
   a. a handle for removably receiving a toothbrush, the handle defining an interior cavity;
   b. a supply of dental floss disposed within the interior cavity of the handle;
   c. means facilitating withdrawal of the dental floss through the handle, said means comprising a floss-receiving aperture through the handle to the interior cavity;
   d. means, associated with the handle, for separating a withdrawn length of dental floss from the supply; and
   e. a flip-out blade assembly including a blade and being pivotally mounted to the handle within the aperture, the blade assembly being (i) pivotable between a closed position wherein the blade is protectively enclosed within the interior cavity and an open position wherein the blade is accessible from outside the handle, and (ii) having an exterior surface cooperating with the pivotal mount so as to permit the blade assembly to be opened or closed by finger pressure applied to the exterior surface.

2. The device of claim 1 wherein the handle is contoured to fit within a user's hand.

3. The device of claim 1 wherein the blade assembly, when in the closed position, closes the aperture and compresses the dental floss received in the aperture to inhibit further withdrawal of the dental floss.

4. The device of claim 1, wherein the handle has a contoured exterior surface and the blade assembly has a smooth exterior surface such that, when the assembly is in its closed position, the assembly's exterior surface follows the exterior surface contour of the handle.

5. The device of claim 1 further comprising means facilitating access to the interior cavity for replacing the supply of dental floss.

* * * * *